US00PP13393P2

(12) United States Plant Patent
Randag

(10) Patent No.: US PP13,393 P2
(45) Date of Patent: Dec. 24, 2002

(54) VARIETY OF CALLA LILY PLANT NAMED 'PURPLE HAZE'

(75) Inventor: Cecilius Jan-Jochem Randag, Schagen (NL)

(73) Assignee: Sande B.V. (NL)

( * ) Notice: Subject to any disclaimer, the term of this patent is extended or adjusted under 35 U.S.C. 154(b) by 0 days.

(21) Appl. No.: 09/494,591

(22) Filed: Jan. 31, 2000

(51) Int. Cl.[7] ..... A01H 5/00
(52) U.S. Cl. ..... Plt./263
(58) Field of Search ..... Plt./263

(56) References Cited

PUBLICATIONS

GTITM UPOVROM Citation for 'Purple Haze' as per NL PBR ARA0164; Dec. 1, 1998.*

* cited by examiner

*Primary Examiner*—Kent L. Bell
(74) *Attorney, Agent, or Firm*—Webb Ziesenheim Logsgon Orkin & Hanson, P.C.

(57) ABSTRACT

'Purple Haze' is a new variety of calla lily having an inflorescence with a purple colored spathe and a yellow and purple colored spadix and producing 1–6 inflorescences per tuber. The leaves are dark green with whitish spots and have a leathery texture.

3 Drawing Sheets

BACKGROUND OF THE NEW PLANT

The present invention comprises a new and distinct cultivar of calla lily, botanically known as *Zantedeschia sprengeri* and hereinafter referred to by the cultivar name 'Purple Haze'.

'Purple Haze' is the product of a planned breeding program which had the objective of creating Zantedschia hybrids for cut flower production in a wide range of colors with a large, classic flower shape. The breeding program began in 1989 and the new cultivar is a seedling selected from the crossing of a *Zantedeschia sprengeri* variety known as 'Cameo', seed parent (unpatented), with a *Zantedeschia sprengeri* variety knows as 'Best Gold', pollen parent (unpatented). 'Purple Haze' was originated in 1995 by the inventor in 't Zand, The Netherlands, as one flowering plant among the progeny of the stated cross. 'Cameo' has pink colored spathes and 'Best Gold' has yellow colored spathes, while 'Purple Haze' has purple colored spathes with yellow edges.

The first act of asexual reproduction of 'Purple Haze' by tissue culture was performed by the inventor in August 1995 in 't Zand, The Netherlands. Subsequent asexual reproduction by tissue culture at the same location has demonstrated that the combination of characteristics as herein disclosed for the new cultivar are retained through successive generations of asexual reproduction.

The following traits have been repeatedly observed and determined to basic characteristics of 'Purple Haze' which, in combination, distinguish this calla lily as a new and distinct cultivar:

1. Purple spathe with a yellow edge;
2. Purple/yellow spadix;
3. Number of inflorescences per tuber.

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

Figure 1:
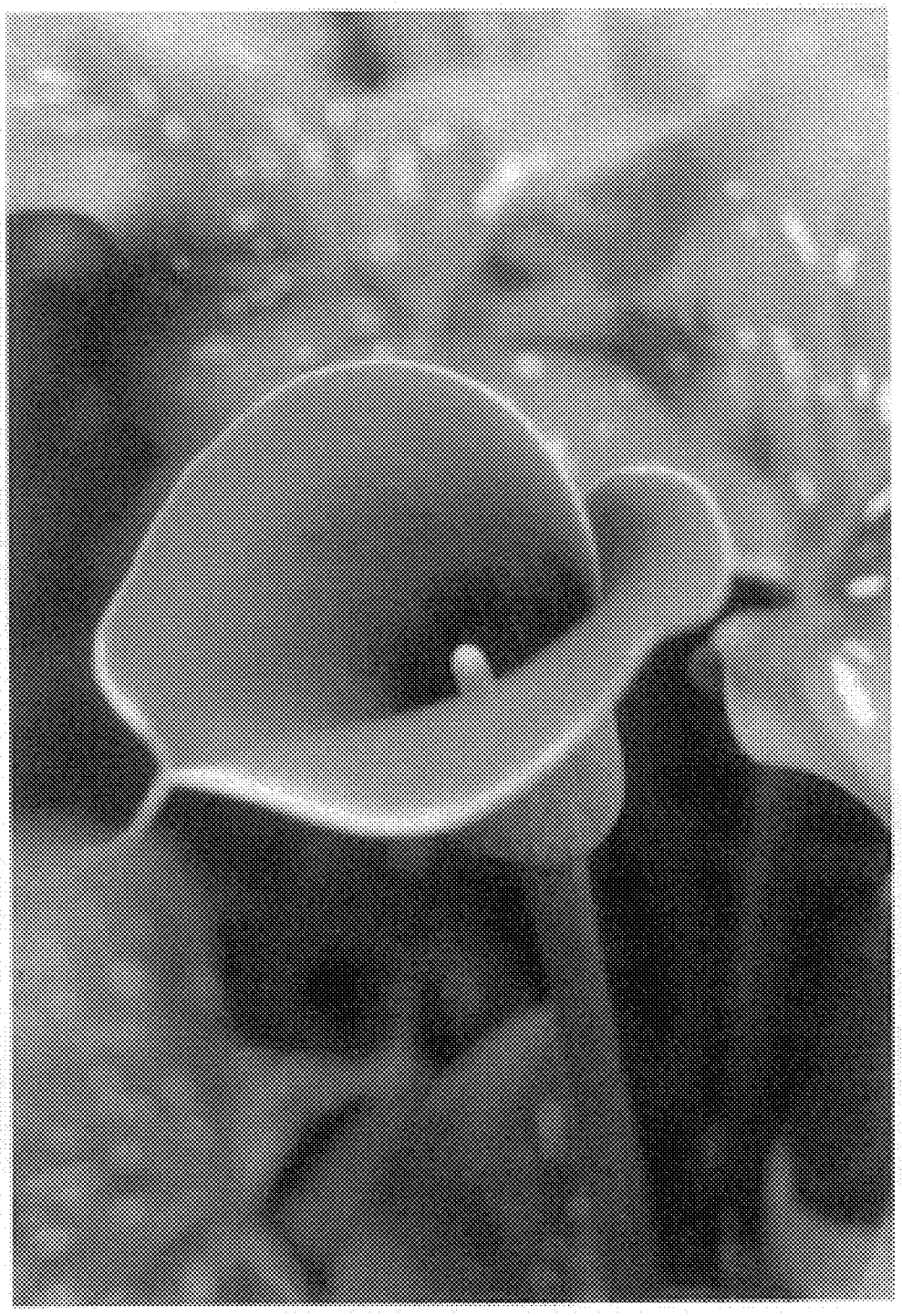
FIG. 1 is a photograph of the inflorescence of 'Purple Haze'.
Figure 2:
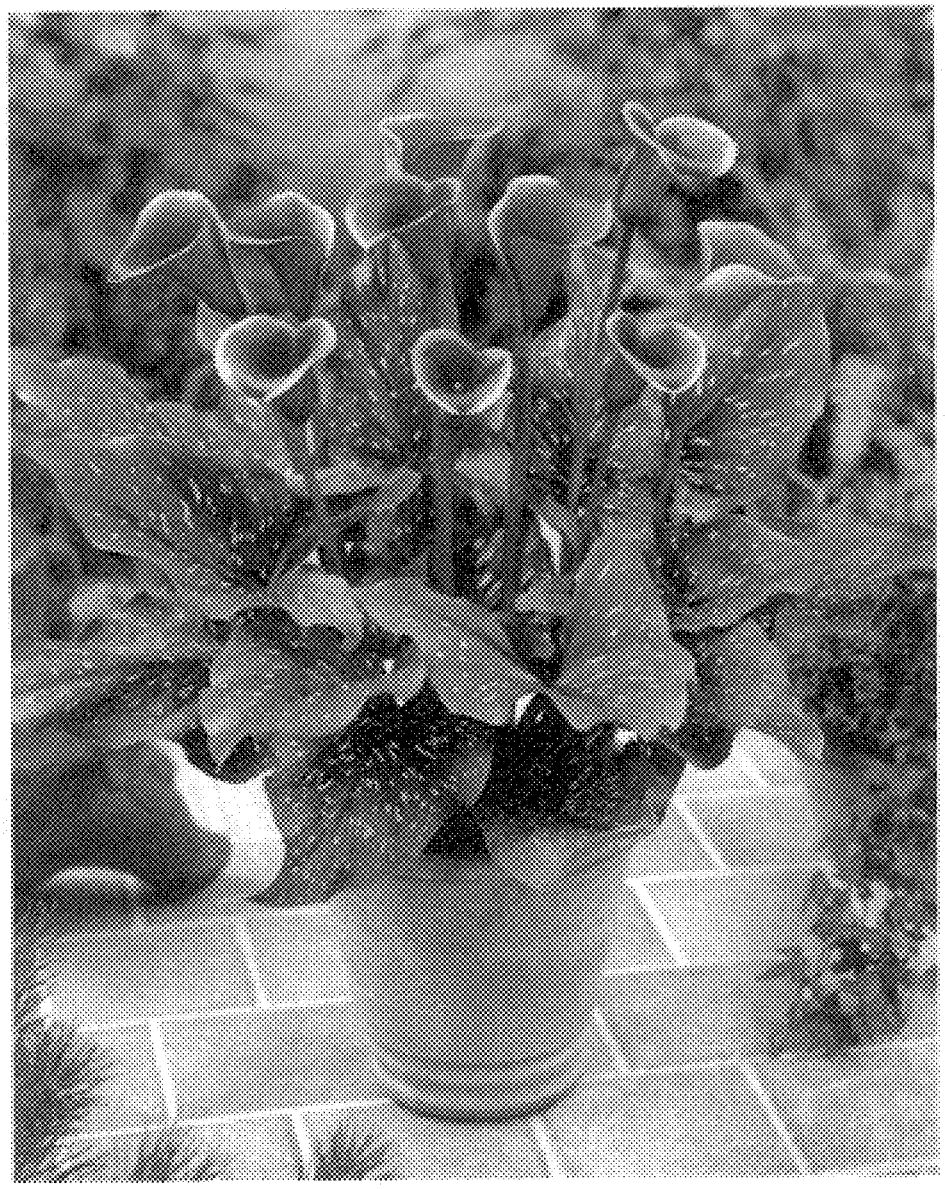
FIG. 2 is a photograph of the 'Purple Haze' plant. Two tubers are in the pot, each with an average of 5 inflorescences per tuber.
Figure 3:
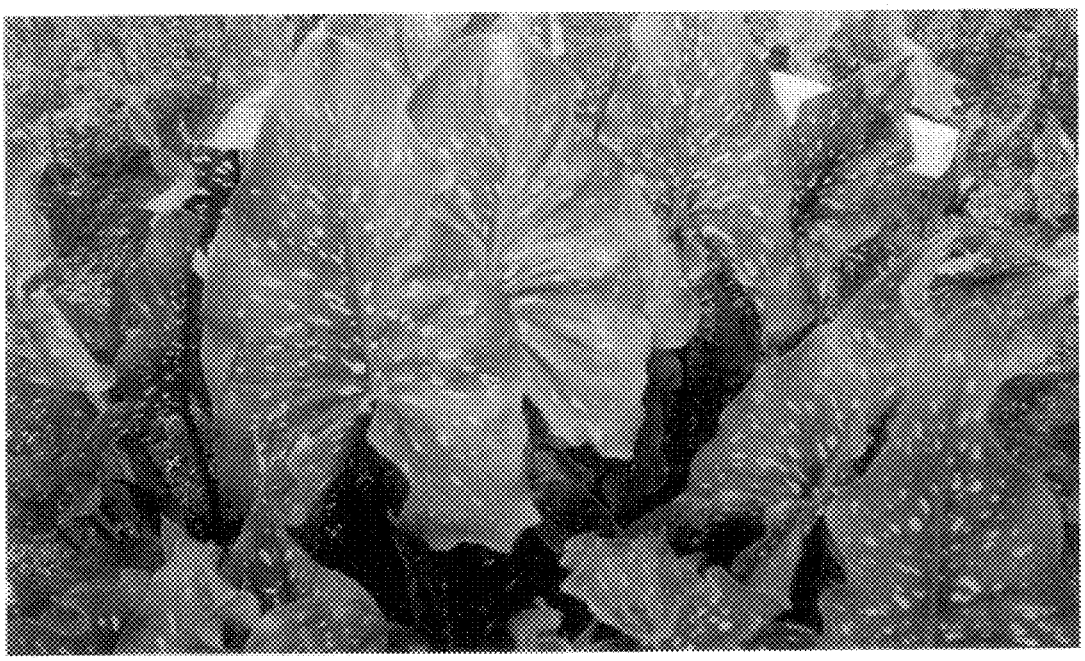
FIG. 3 is a photograph of the leaves of the 'Purple Haze' plant.

The following observations, measurements and comparisons decsribe plants grown in 't Zand, The Netherlands under greenhouse conditions which approximate those generally used in horticultural practice. Age of the observed plant was two years after tissue culture. The observed plant was grown in a container with an 18 cm diameter. Color references are made to The R.H.S. Colour Chart of The Royal Horticultural Society of London, except where general color terms of ordinary significance are used.

THE PLANT

Size:
- *Height of the leaf canopy above the soil.*—60–75 cm.
- *Height of top of inflorescence above the soil.*—60–80 cm.
- *Diameter.*—40–50 cm.
- *Form.*—Erect.

Number of inflorescences per tuber size:
- *Length 9–12 cm.*—1–2 inflorescences.
- *Length 12–15 cm.*—2–3 inflorescences.
- *Length 15–18 cm.*—3–6 inflorescences.

Branches:
- *Character.*—Strong.
- *Color.*—Upper part Yellow-Green Group 146B, lower part Greyed-Purple Group 183A, bases White Group 155B.
- *Average number.*—3–4 branches on a 15–18 cm tuber.

Leaves:
- *Size.*—Width: 25 cm. Length: 30 cm.
- *Shape.*—Heart shaped.

*Color.*—Upper surface: Green Group 139A. Lower surface: Varies between Yellow-Green Groups 146A–146B. Spots (masculation): White Group 155C.

*Apex.*—Acute to apiculate.

*Margin.*—Wavy; entire.

*Veins.*—Configuration: Pinnate. Color: Yellow-Green Group 146D.

*Surface quality.*—Leathery.

Petiole:

*Length.*—40 cm.

*Color.*—Base is Greyed-Purple Group 183A, upper part varies between Yellow-Green Groups 146A–146B.

Roots:

*Color.*—White.

*Branching.*—Not branched; roots are attached directly to the tuber.

Disease resistance: No susceptibility to disease noted to date.

Pest resistance: No susceptibility to pests noted to date.

THE INFLORESCENCE

Spathe:

*Size.*—Length: 8–10 cm. Width: 7–9 cm.

*Color.*—Upper surface: Red-Purple Group between 64A and 71A with a yellow edge Yellow Group 9B. Lower surface: Red-Purple Group between 64A and 71A. Apex: Apiculate. Margin: Entire.

*Veins.*—Color: Red-Purple Group 64A or Yellow Group 9B.

*Shape.*—Cupped.

Spadix:

*Size.*—Length: 5.0–5.5 cm. Diameter: 0.6–1.0 cm.

*Color.*—Yellow-Orange Group 17A with a few spots of Red-Purple Groups 64A and 71A.

*Position relative to spathe.*—Upright.

Peduncle:

*Size.*—Length: 60 cm. Diameter: 12 mm.

*Color.*—Base is Greyed-Purple Group 183A, upper part varies between Yellow-Green Groups 146A–146B.

Reproductive organs:

*Location of female organs.*—Basal position of the spadix.

*Location of male organs.*—Upper position of the spadix.

*Perianth.*—Conspicuous.

*Stamens.*—Not visible before pollen release.

Pistil.—Amount: 30–60 per spadix. Color: Yellow-Green Group 151D. Length beyond perianth: About 1 mm.

Flowering: Tubers planted in a greenhouse in The Netherlands in February produce flowers in April. Tubers planted outdoors in The Netherlands in May produce flowers in July.

Lastingness: About two weeks on the plant.

Fragrance: None.

Fruit:

*Production.*—30–60 berries.

*Color.*—Yellow-Green Group 144A berries.

I claim:

1. A new and distinct variety of calla lily plant named 'Purple Haze' as described and illustrated.

* * * * *

UNITED STATES PATENT AND TRADEMARK OFFICE

CERTIFICATE OF CORRECTION

PATENT NO. : PP 13,393 P2
DATED : December 24, 2002
INVENTOR(S) : Cecilius Jan-Jochem Randag It is certified that error appears in the above-identified patent and that said Letters Patent is hereby corrected as shown below:

Column 3,
Line 3, "(masculation)" should read -- (maculation) --.

Signed and Sealed this

Tenth Day of June, 2003

JAMES E. ROGAN
*Director of the United States Patent and Trademark Office*